(12) United States Patent
Ishiwata (10) Patent No.: US 8,740,615 B2
(45) Date of Patent: Jun. 3, 2014

(54) IMPLANT, IMPLANT BODY, AND ABUTMENT BODY

(75) Inventor: Teruo Ishiwata, Numazu (JP)

(73) Assignee: Nanto. Precision Co., Ltd, Shizuoka (JP)

( * ) Notice: Subject to any disclaimer, the term of this patent is extended or adjusted under 35 U.S.C. 154(b) by 0 days.

(21) Appl. No.: 13/883,249

(22) PCT Filed: Nov. 24, 2011

(86) PCT No.: PCT/JP2011/077016
§ 371 (c)(1),
(2), (4) Date: May 2, 2013

(87) PCT Pub. No.: WO2012/070606
PCT Pub. Date: May 31, 2012

(65) Prior Publication Data
US 2013/0224689 A1    Aug. 29, 2013

(30) Foreign Application Priority Data

Nov. 26, 2010   (JP) ................................. 2010-264206

(51) Int. Cl.
*A61C 8/00* (2006.01)

(52) U.S. Cl.
USPC ........................................................ 433/173

(58) Field of Classification Search
USPC ...................... 433/172–176, 201.1
See application file for complete search history.

(56) References Cited

U.S. PATENT DOCUMENTS

| 5,733,122 A | 3/1998 | Gordon |
| 5,782,918 A | 7/1998 | Klardie et al. |
| 2008/0182227 A1 | 7/2008 | Wolf |
| 2010/0304334 A1 * | 12/2010 | Layton ......................... 433/173 |

FOREIGN PATENT DOCUMENTS

| EP | 1 021 996 A1 | 7/2000 |
| EP | 1 702 581 A1 | 9/2006 |
| JP | 08-196548 A | 8/1996 |
| JP | 2003-052720 A | 2/2003 |
| JP | 2004-113718 | 4/2004 |
| JP | 2008-52819 A | 7/2008 |
| JP | 2010-046153 A | 3/2010 |

OTHER PUBLICATIONS

International Search Report, PCT/JP2011/077016, dated Jan. 10, 2012.
Extended Search Report in European Patent Application No. 11842698.0, mailed on Mar. 13, 2014.

* cited by examiner

*Primary Examiner* — Eric Rosen
(74) *Attorney, Agent, or Firm* — Nixon Peabody LLP (57) ABSTRACT

An implant that includes an implant body in which a fitting hole portion having a taper shape is formed, and an abutment having a fitting shaft portion having a taper shape. A pressure-withstanding mechanism configured by the fitting hole portion and the fitting shaft portion and a rotation-preventing mechanism preventing rotation of the abutment with respect to the implant body are integrally formed.

7 Claims, 11 Drawing Sheets

VIb-VIb

IXb-IXb

IMPLANT, IMPLANT BODY, AND ABUTMENT BODY

CROSS REFERENCE TO RELATED APPLICATIONS OR PRIORITY CLAIM

This application is a National Phase of PCT/JP2011/0077016, filed Nov. 24, 2011, entitled, "IMPLANT, IMPLANT BODY, ABUTMENT BODY," which claims the benefit of Japanese Patent Application No. 2010-264206, filed Nov. 26, 2010, the contents of which are incorporated herein by reference in their entirety.

TECHNICAL FIELD

The present invention relates to an implant, an implant body, and an abutment body. The present invention relates to a dental implant or the like that is embedded into the jaw bone at the time of, for example, tooth root loss or the like of a permanent tooth.

BACKGROUND ART

An implant that is embedded into the body (in particular, a dental implant) is attracting attention. In the dental implant, generally, in a case where the tooth root of a permanent tooth has been lost due to dental caries or damage, an implant body is inserted into and fixed to a hole provided at the alveolar bone. The dental implant is configured to include an implant body that is fixed to the alveolar bone, and an abutment which is screwed into the implant body and on which an artificial crown can be mounted.

An implant body described in PTL 1 has a hole portion which is opened at an upper end face thereof. In the hole portion, a hexagonal hole portion and a tapered hole portion are formed. In the implant body, a hexagonal shaft portion that is inserted into the hexagonal hole portion and a tapered shaft portion that comes into contact with the tapered hole portion are formed.

The hexagonal hole portion and the hexagonal axis portion become a rotation-preventing portion. The rotation-preventing portion prevents rotation around a vertical direction with respect to occlusal pressure. The rotation-preventing portion prevents rotation of an abutment with respect to the implant body.

The tapered hole portion and the tapered shaft portion are provided in order to take the occlusal pressure. The tapered hole portion and the tapered shaft portion are formed adjacent to the rotation-preventing portion (the hexagonal hole portion and the hexagonal axis portion).

The tapered shaft portion is fitted into the tapered hole portion in a wedge form by inserting the abutment into the hole portion of the implant body.

CITATION LIST

Patent Literature

PTL 1: Japanese Unexamined Patent Application, First Publication No. 2004-113718

SUMMARY OF INVENTION

Technical Problem

In the related art, there are the following problems. In an implant described in PTL 1, since the occlusal pressure is concentrated on tapered portions (the tapered hole portion and the tapered shaft portion) provided in order to take the occlusal pressure, a crack is generated in the tapered hole portion or the like of the implant body. In the worst case scenario, the implant body is broken. Further, if the rotation-preventing portion having a hexagonal shape repeatedly receives the occlusal pressure, vertex portions of the hexagonal shape are worn out, and thus rattling is gradually generated.

As a material of the abutment, pure titanium is often adopted. Black titanium is reflected on the surface of an artificial bone, and thus the aesthetics is inferior. In a case where a gum drops after surgery, the abutment is exposed, and thus there is a problem in that the titanium color is conspicuous and the aesthetics is inferior. Therefore, it is considered to form the abutment by using white ceramic having excellent aesthetics.

However, in a fixing method in which a screw structure is provided in the abutment itself, since ceramics such as zirconia have a very high hardness, there is a concern that a screw may be damaged at the time of fastening.

An object of the present invention is to provide an implant, an implant body, and an abutment body which have structures in which even if they receive high occlusal pressure, a crack or the like is not easily generated, and in which rotation of an abutment with respect to the implant body can be stably prevented over a long period of time.

Solution to Problem

According to an aspect of the invention, an implant is provided, including: an implant body in which a fitting hole portion having a taper shape, an inner diameter of which is reduced over a depth direction, is formed in a portion of a central hole; and an abutment having a fitting shaft portion having a taper shape, which is fitted into the fitting hole portion, wherein a pressure-withstanding mechanism that is configured by the fitting hole portion and the fitting shaft portion and a rotation-preventing mechanism that prevents rotation of the abutment with respect to the implant body are integrally formed.

The length of the pressure-withstanding mechanism may be formed to be a length of ⅓ or more of the overall length of the implant body.

The rotation-preventing mechanism may include: a plurality of protrusion portions formed along the depth direction on an inner peripheral surface of the fitting hole portion; and a plurality of groove portions which is formed along an axial direction in an outer peripheral surface of the fitting shaft portion and into which the plurality of protrusion portions is respectively inserted.

Each of the cross-sectional shape perpendicular to the depth direction of each of the plurality of protrusion portions and the cross-sectional shape perpendicular to the axial direction of each of the plurality of groove portions may be formed in an arc shape.

The implant may further include: a clamper pin which is inserted into a through-hole formed along the axial direction of the abutment and has a co-rotation restriction shaft portion which is engaged with a co-rotation restriction hole portion formed in the central hole of the implant body such that rotation around an axis is restricted; a lock nut which has an external thread that is screwed in an internal thread formed at a portion of the through-hole of the abutment and an internal thread that is screwed in an external thread formed at a portion of the clamper pin and which relatively moves the clamper pin and the abutment; and a clamper which is interposed between the clamper pin and the central hole of the implant body and engaged with a separation prevention shaft portion of the clamper pin and a separation prevention hole portion of the implant body according to relative movement of the clamper pin and the abutment, thereby restricting relative movement of the clamper pin and the implant body.

Each of the implant body and the abutment may be formed of ceramic.

Each of the implant body and the abutment may be formed of zirconia.

Each of the clamper pin, the clamper, and the lock nut may be formed of titanium or titanium alloy.

According to another aspect to the invention, an implant body is provided in which an abutment body is fitted into a central hole, wherein the central hole has a taper shape, an inner diameter of which is reduced over a depth direction, and has a fitting hole portion in which a plurality of protrusion portions following the depth direction is formed on an inner peripheral surface.

According to still another aspect to the invention, an abutment body is provided that is fitted into a central hole of an implant body, the abutment body including: a tapered shaft portion, an outer diameter of which is reduced over an axial direction, and in which a plurality of groove portions following the axial direction is formed in an outer peripheral surface.

The abutment body may further include: an abutment in which the tapered shaft portion is formed; a clamper pin which is inserted into a through-hole formed along the axial direction of the abutment and has a co-rotation restriction shaft portion that is engaged with a co-rotation restriction hole portion formed in the central hole of the implant body such that rotation around an axis is restricted; a lock nut which has an external thread that is screwed in an internal thread formed at a portion of the through-hole of the abutment and an internal thread that is screwed in an external thread formed at a portion of the clamper pin, and which relatively moves the clamper pin and the abutment; and a clamper which is interposed between the clamper pin and the central hole of the implant body and engaged with a separation prevention shaft portion of the clamper pin and a separation prevention hole portion of the implant body according to the relative movement of the clamper pin and the abutment, thereby restricting relative movement of the clamper pin and the implant body.

Advantageous Effects of Invention

The implant, the implant body, and the abutment body according to the invention have structures in which even if they receive occlusal pressure, a crack is not easily generated. Further, rotation of an abutment with respect to the implant body can be stably prevented over a long period of time.

DESCRIPTION OF EMBODIMENTS

An embodiment of the invention will be described referring to the drawings. Various dimensions or the like shown in the following description are examples.

Dental Implant

Figure 1:
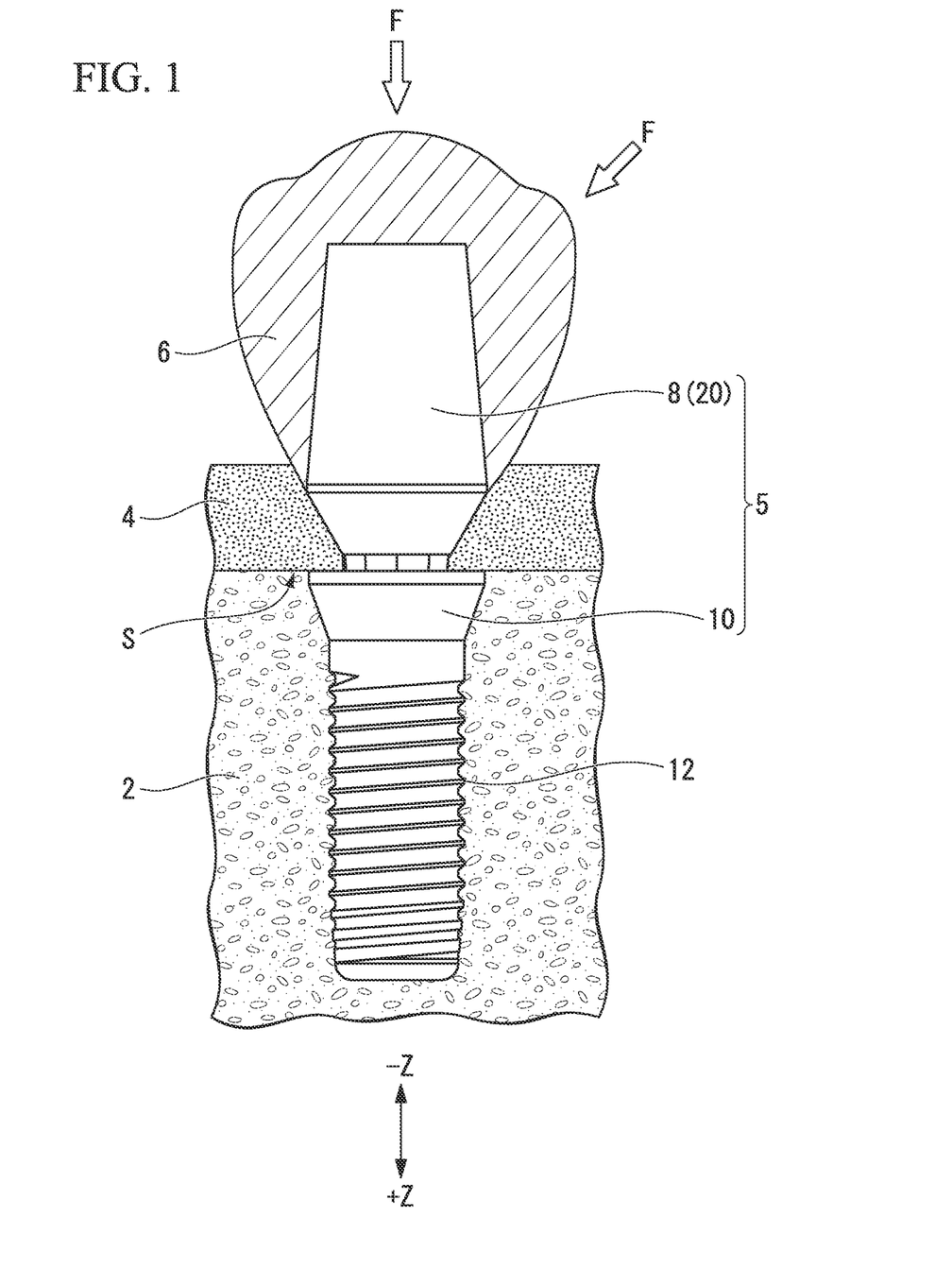
FIG. 1 is a diagram showing an example of use in the field of dentistry of an implant related to an embodiment of the invention.

FIG. 1 is a diagram showing an example of use in the field of dentistry of an implant 5 related to the embodiment of the invention.

The implant 5 includes an implant body 10 which is fixed to an alveolar bone 2, and an abutment body 8 detachable with respect to the implant body 10. An artificial crown 6 is mounted on the abutment body 8.

A male screw 12 is formed in the outer peripheral surface of the implant body 10. The implant body 10 is fixed to the alveolar bone 2 by screwing the male screw 12 into a hole formed in the alveolar bone 2.

The artificial crown 6 is mounted on the outer peripheral surface of the abutment body 8 by using an adhesive or the like. A contact section S between the implant body 10 and the abutment body 8 is covered by a gum 4 or the alveolar bone 2.

The contact surfaces in the contact section S of the implant body 10 and the abutment body 8 are accurately finished. The contact surfaces come into close contact with each other to prevent intrusion of a foreign material.

Figure 2:
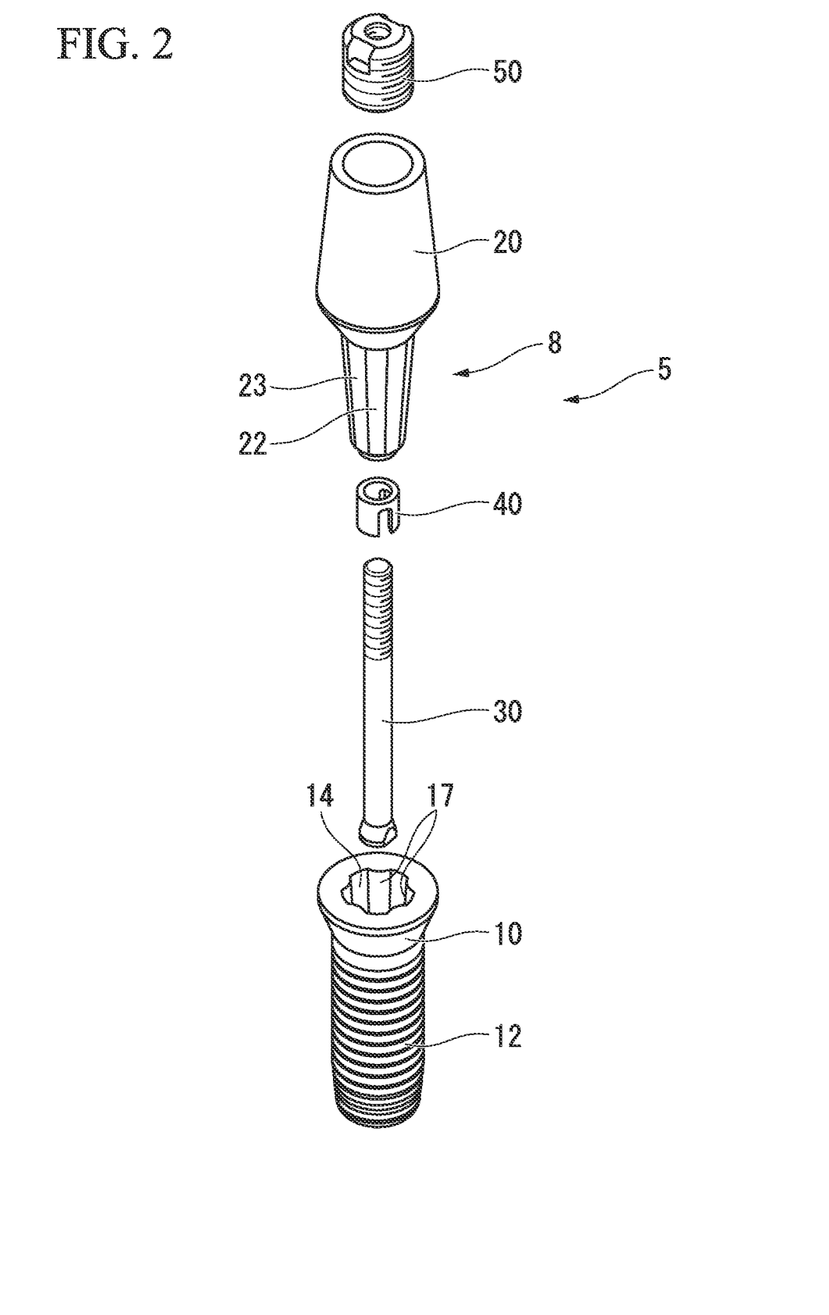
FIG. 2 is an exploded perspective view of the implant related to the embodiment of the invention.
Figure 3:
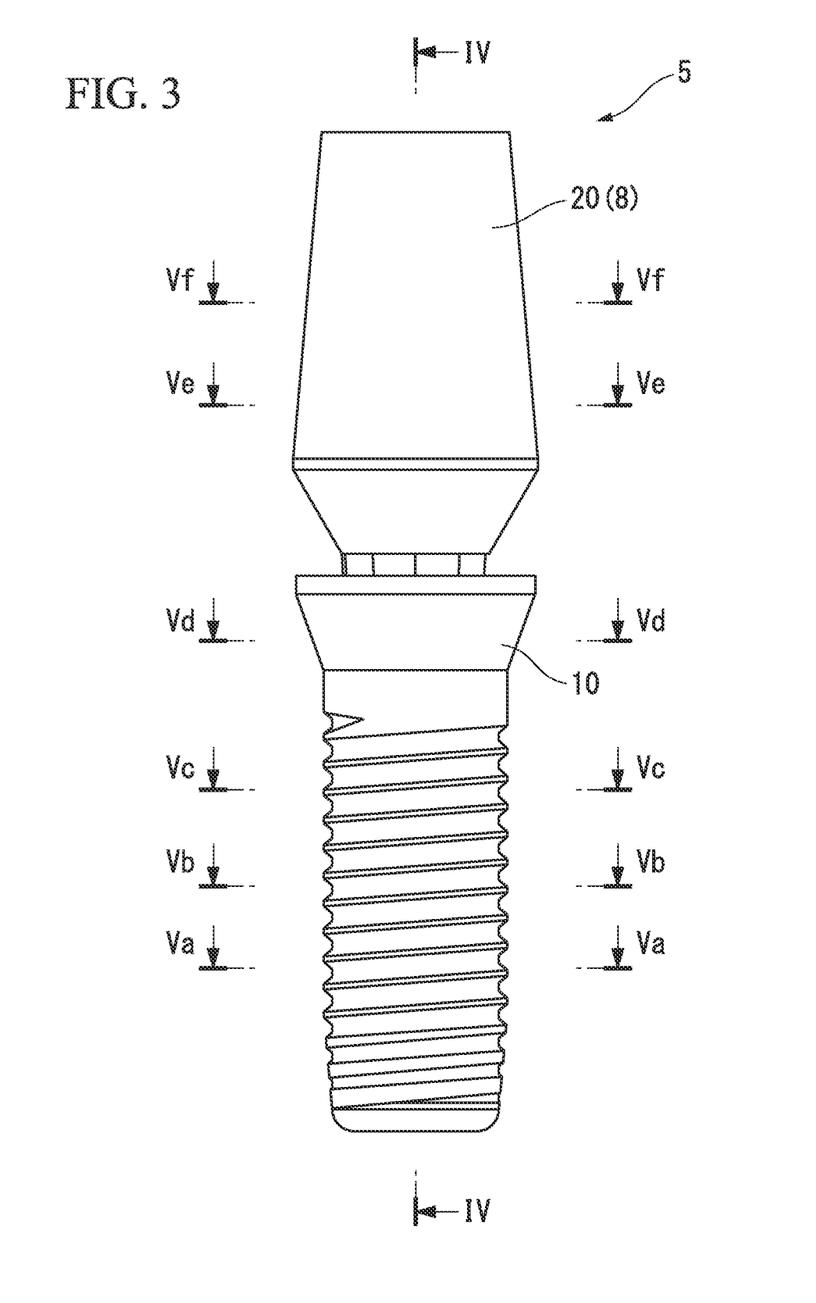
FIG. 3 is a side view of the implant.
Figure 4:
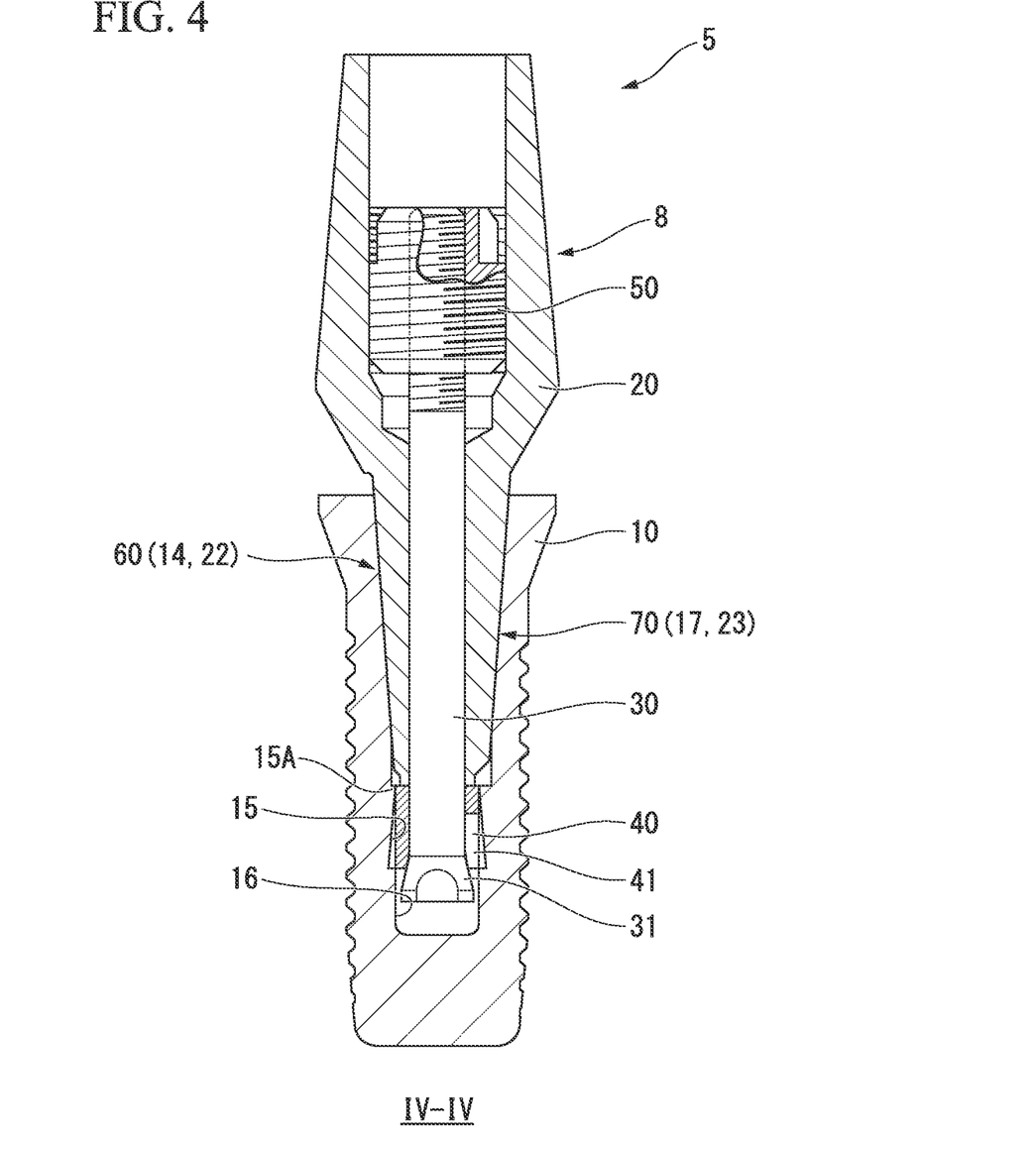
FIG. 4 is a longitudinal cross-sectional view (a cross-section along line IV-IV of FIG. 3) of the implant.
Figure 5A:
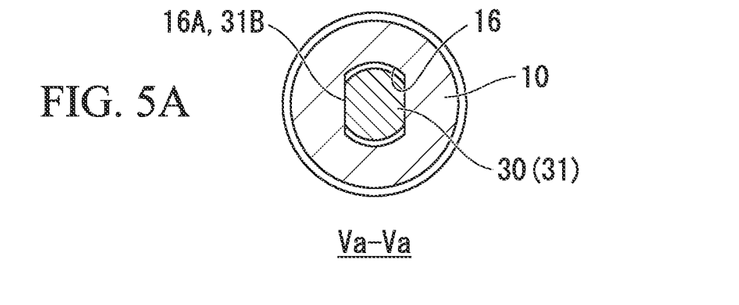
FIG. 5A is a transverse cross-sectional view (a cross-section along line Va-Va of FIG. 3) of the implant.
Figure 5B:
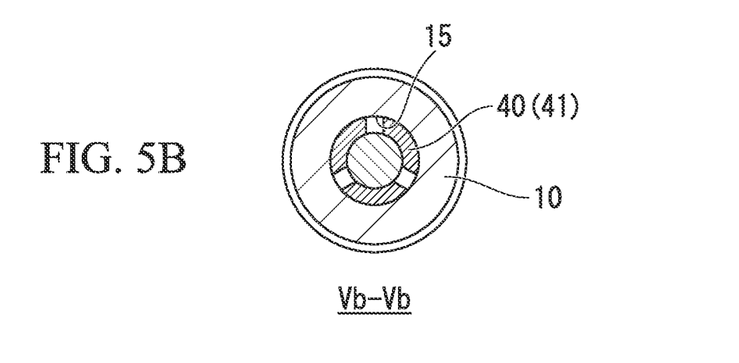
FIG. 5B is a transverse cross-sectional view (a cross-section along line Vb-Vb of FIG. 3) of the implant.
Figure 5C:
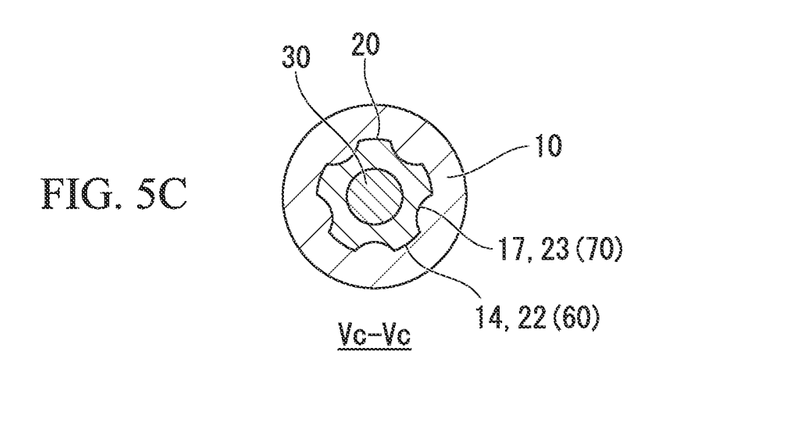
FIG. 5C is a transverse cross-sectional view (a cross-section along line Vc-Vc of FIG. 3) of the implant.
Figure 5D:
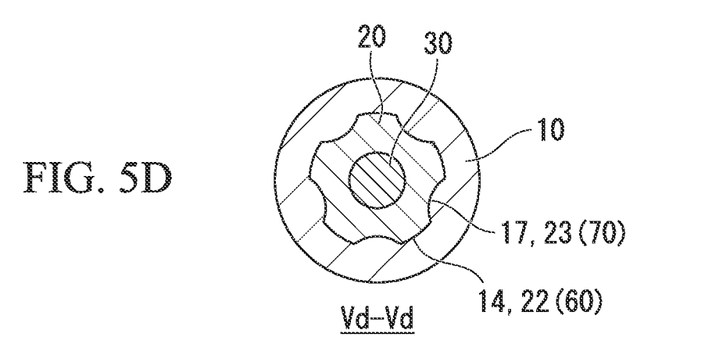
FIG. 5D is a transverse cross-sectional view (a cross-section along line Vd-Vd of FIG. 3) of the implant.
Figure 5E:
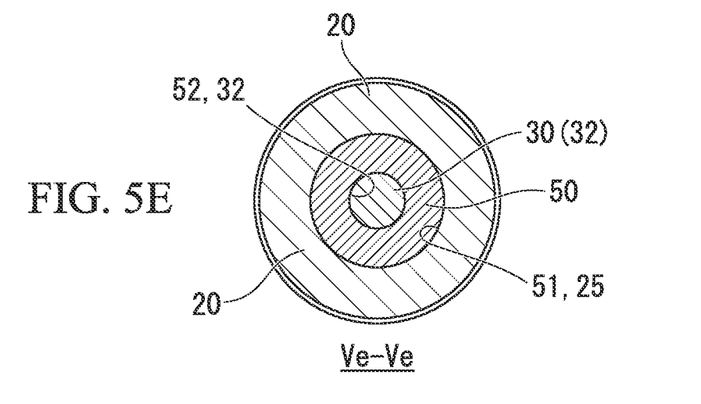
FIG. 5E is a transverse cross-sectional view (a cross-section along line Ve-Ve of FIG. 3) of the implant.
Figure 5F:
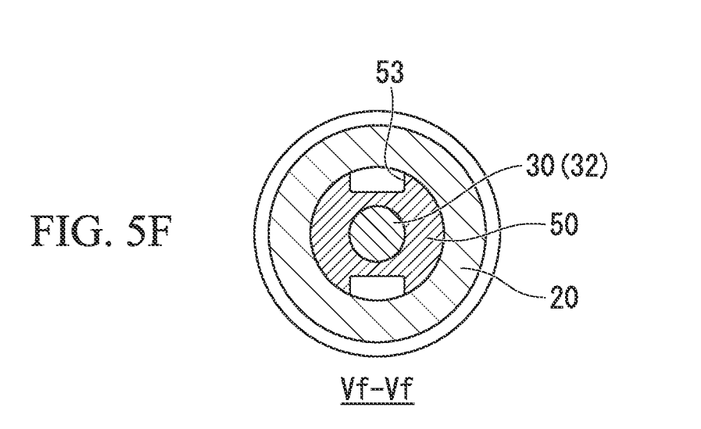
FIG. 5F is a transverse cross-sectional view (a cross-section along line V-Vf of FIG. 3) of the implant.

FIG. 2 is an exploded perspective view of the implant 5 related to the embodiment of the invention. FIG. 3 is a side view of the implant 5. FIG. 4 is a longitudinal cross-sectional view (a cross-section along line IV-IV of FIG. 3) of the implant 5. FIGS. 5A to 5F are transverse cross-sectional views of the implant 5. FIG. 5A shows a cross-section along line Va-Va of FIG. 3, FIG. 5B shows a cross-section along line Vb-Vb of FIG. 3, FIG. 5C shows a cross-section along line Vc-Vc of FIG. 3, FIG. 5D shows a cross-section along line Vd-Vd of FIG. 3, FIG. 5E shows a cross-section along line Ve-Ve of FIG. 3, and FIG. 5F shows a cross-section along line Vf-Vf of FIG. 3.

The implant 5 includes the implant body 10 and the abutment body 8.

The abutment body 8 is an assembly of an abutment 20, a clamper pin 30, a clamper 40, and a lock nut 50.

The abutment body 8 includes the abutment 20 that is a shaft-shaped member, the clamper pin 30 having a shaft shape, the clamper 40 having a ring shape, and the lock nut 50. The artificial crown 6 is mounted on the abutment 20. The clamper pin 30 is inserted into a through-hole 24 of the abutment 20. The clamper pin 30 is engaged with the implant body 10. The clamper 40 is fitted onto the clamper pin 30. The lock nut 50 is screwed into the abutment 20 and onto the clamper pin 30.

The central axis of the clamper pin 30 is set to be a Z axis (a Z direction, a depth direction, or an axial direction). The implant body 10 side is set to be a +Z side (a +Z direction). The abutment 20 side is set to be a −Z side (a −Z direction). A top view is set when viewed from the −Z direction and a bottom view is set when viewed from the +Z direction.

Figure 6A:
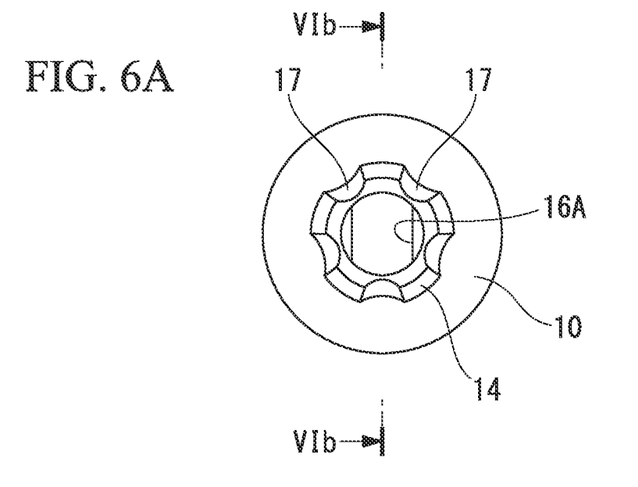
FIG. 6A is a top view showing an implant body related to the embodiment of the invention.
Figure 6B:
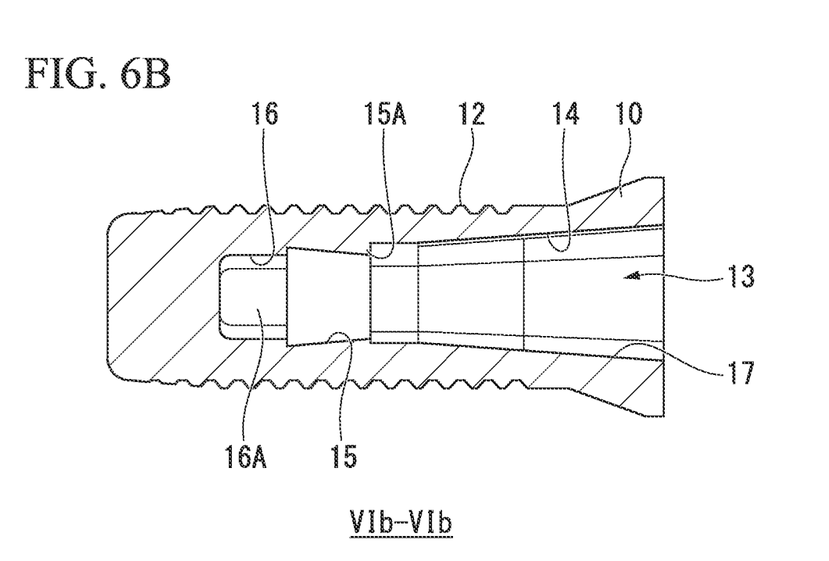
FIG. 6B is a longitudinal cross-sectional view (a cross-section along line VIb-VIb of FIG. 6A) showing the implant body related to the embodiment of the invention.

FIG. 6A is a top view showing the implant body 10 related to the embodiment of the invention, and FIG. 6B is a longitudinal cross-sectional view (a cross-section along line VIb-VIb of FIG. 6A) showing the implant body 10 related to the embodiment of the invention.

The implant body 10 is a shaft-shaped member formed of a ceramic material such as zirconia. The implant body 10 is also called a fixture. The implant body 10 is formed in a columnar shape and the male screw 12 is formed in the outer peripheral surface thereof.

A central hole 13 is opened at the center of the end face on the −Z side of the implant body 10. In the central hole 13, a tapered hole portion 14, an inverse tapered hole portion 15, and an engagement hole portion 16 are continuous toward the +Z side. The tapered hole portion 14 has an inner diameter that is gradually reduced (reduced in diameter) toward the +Z side from the end face on the −Z side. The inverse tapered hole portion 15 has an inner diameter that is gradually enlarged (enlarged in diameter) toward the +Z side. In the engagement hole portion 16, two parallel faces 16A are formed of two inner side surfaces parallel to each other and facing each other.

The taper angle of the tapered hole portion 14 is, for example, 8°. The average diameter of the tapered hole portion 14 is, for example, 2 mm. The length (the depth) of the tapered hole portion 14 is formed to be a length (for example, a range of 4 to 5 mm) of ⅓ or more of the overall length (for example, 10 mm) of the implant body 10.

A plurality of projections 17 (protrusion portions) following the Z direction is formed on the inner peripheral side surface of the tapered hole portion 14. The plurality of projections 17 (protrusion portions) is disposed at equal intervals (equal angles) in the circumferential direction of the central hole 13. The projection 17 is, for example, five.

The shape of the cross-section perpendicular to the Z axis of the projection 17 is an inverted U-shape. The top side of the projection 17 has an arc shape.

The minimum inner diameter of the inverse tapered hole portion 15 is smaller than the minimum inner diameter of the tapered hole portion 14. A protruding site (a separation prevention hole portion) 15A protruding to the inner periphery side of the central hole 13 is formed at a connection portion between the tapered hole portion 14 and the inverse tapered hole portion 15. The taper angle of the inverse tapered hole portion 15 is, for example, 10°. The length (the depth) of the inverse tapered hole portion 15 is, for example, 2.5 mm.

The engagement hole portion 16 is configured by two arc inner peripheral side surfaces facing each other and two inner side surfaces parallel to and facing each other. The two inner side surfaces are the two parallel faces (a co-rotation restriction hole portion) 16A. The length (the depth) of the engagement hole portion 16 is, for example, 1.2 mm. The width of each of the two parallel faces 16A (width across flats) is about 1.1 mm.

Figure 7A:
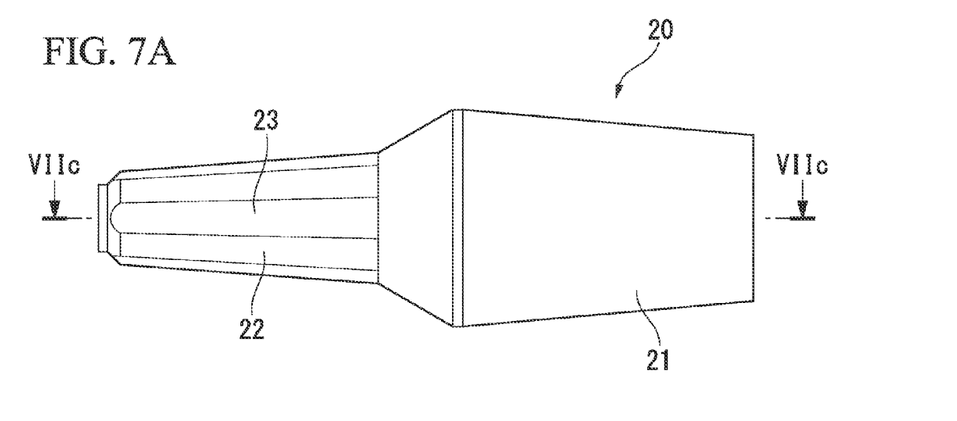
FIG. 7A is a side view showing an abutment related to the embodiment of the invention.
Figure 7B:
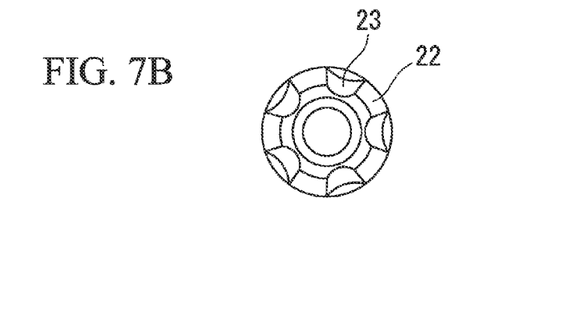
FIG. 7B is a bottom view showing the abutment related to the embodiment of the invention.
Figure 7C:
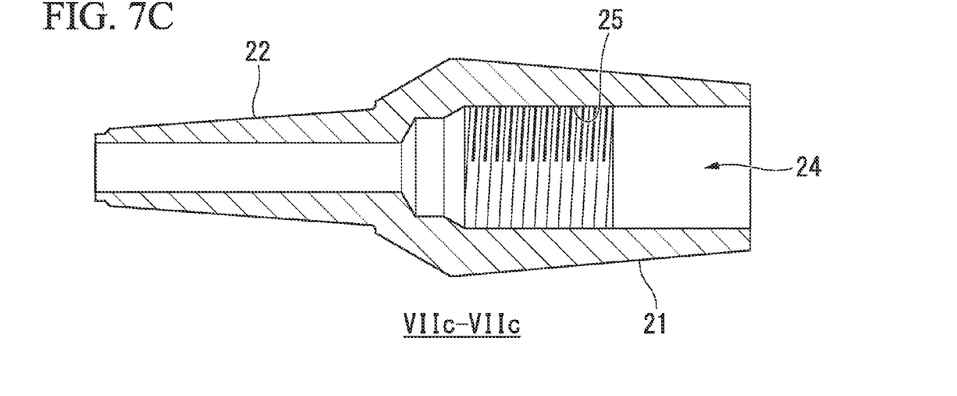
FIG. 7C is a longitudinal cross-sectional view (a cross-section along line VIIc-VIIc of FIG. 7A) showing the abutment related to the embodiment of the invention.

FIG. 7A is a side view showing the abutment 20 related to the embodiment of the invention. FIG. 7B is a bottom view showing the abutment 20 related to the embodiment of the invention. FIG. 7C is a longitudinal cross-sectional view (a cross-section along line VIIc-VIIc of FIG. 7A) showing the abutment 20 related to the embodiment of the invention.

The abutment 20 includes a main body portion 21 on which the artificial crown 6 is mounted, and a tapered shaft portion 22 that is provided to extend from 1st end side (the +Z side) of the main body portion 21. The tapered shaft portion 22 is inserted into the central hole 13 of the implant body 10.

The abutment 20 is integrally formed of a white ceramic material having excellent aesthetics. As the ceramic material, zirconia is adopted.

The taper angle of the tapered shaft portion 22 is, for example, 8° and is the same as the angle of the tapered hole portion 14 of the central hole 13 of the implant body 10.

The average inner diameter of the tapered shaft portion 22 is, for example, 2 mm. The length of the tapered shaft portion 22 is formed to be the same as or be longer than that of the tapered hole portion 14. The length of the tapered shaft portion 22 is, for example, 6 mm.

A plurality of groove portions 23 is formed along the Z direction in the outer peripheral side surface of the tapered shaft portion 22. The plurality of groove portions 23 is disposed at equal intervals (equal angles) in the circumferential direction of the tapered shaft portion 22. The number of groove portions 23 is five and is the same as the number of projections 17 which is formed in the inner peripheral side surface of the tapered hole portion 14.

The shape of the cross-section perpendicular to the Z axis of the groove portion 23 is an inverted U-shape. The top side of the groove portion 23 has an arc shape which is the same shape as that of the projection 17 formed on the inner peripheral side surface of the tapered hole portion 14.

When the abutment 20 is inserted into the central hole 13 of the implant body 10, the tapered shaft portion 22 of the abutment 20 is fitted into the tapered hole portion 14 of the central hole 13 of the implant body 10. At this time, the five groove portions 23 formed on the tapered shaft portion 22 are inserted into the five projections 17 formed on the tapered hole portion 14.

The through-hole 24 penetrating in the Z direction is formed at the center of the abutment 20. A site of the through-hole 24, corresponding to the main body portion 21, is formed so as to have an inner diameter of about 2.5 mm. An internal thread 25 having a screw standard of M2.5 is provided at a portion of the through-hole 24. The screw dimension or the like of the internal thread 25 can be appropriately changed according to the inner diameter or the like of the through-hole 24.

A site of the through-hole 24, corresponding to the tapered shaft portion 22, is formed so as to have an inner diameter of about 1 mm. The clamper pin 30 is inserted into the through-hole 24 almost without clearance.

Figure 8A:
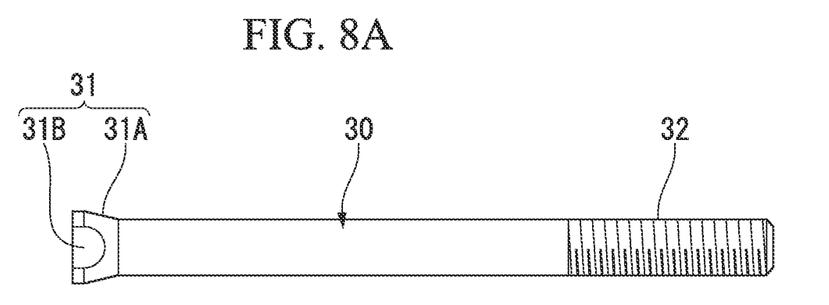
FIG. 8A is a side view showing a clamper pin.
Figure 8B:
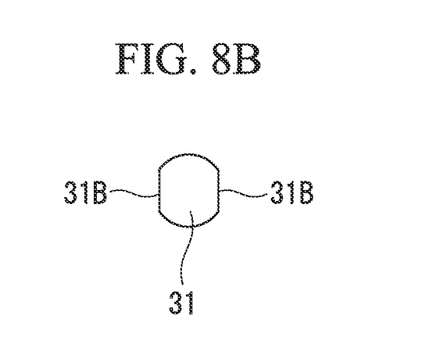
FIG. 8B is a bottom view showing the clamper pin.

FIG. 8A is a side view showing the clamper pin 30. FIG. 8B is a bottom view showing the clamper pin 30.

The clamper pin 30 is an elongated shaft-shaped member. The clamper pin 30 is formed of titanium or titanium alloy. The diameter of the clamper pin 30 is about 1 mm.

An engagement portion 31 is provided on 1st end side (the +Z side) of the clamper pin 30. The engagement portion 31 is fitted into the engagement hole portion 16 formed in the deepest portion of the central hole 13 of the implant body 10.

The engagement portion 31 is configured by a tapered site 31A and two parallel faces 31B. The tapered site 31A has an outer diameter that is gradually enlarged (enlarged in diameter) toward the +Z side. The two parallel faces 31B are two faces parallel to each other and facing in the opposite directions, which are formed on the outer surface of the tapered site 31A.

The angle of the tapered site (a separation prevention shaft portion) 31A is about 30°. The width of each of the two parallel faces (a co-rotation restriction shaft portion) 31B (the two-face width) is about 1.1 mm.

An external thread 32 having a screw standard of M1 is provided on 2nd end side (the −Z side) of the clamper pin 30. The screw dimension or the like of the external thread 32 can be appropriately changed according to the diameter or the like of the clamper pin 30.

The length of the clamper pin 30 is a length in which when the implant 5 has been assembled, the external thread 32 is located at almost the same position as the internal thread 25 of the end portion (the −Z side) of the through-hole 24 of the abutment 20.

Figure 9A:
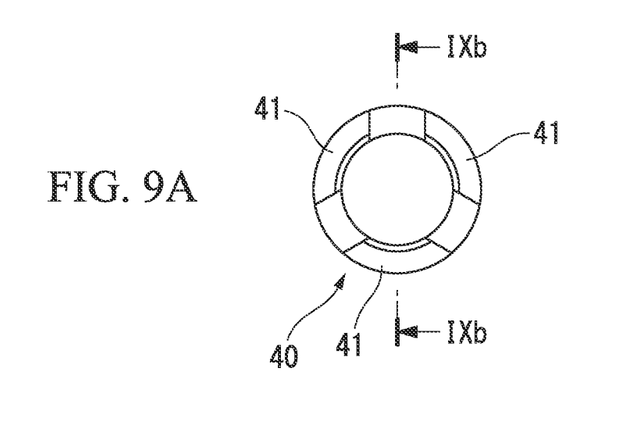
FIG. 9A is a bottom view showing a clamper.
Figure 9B:
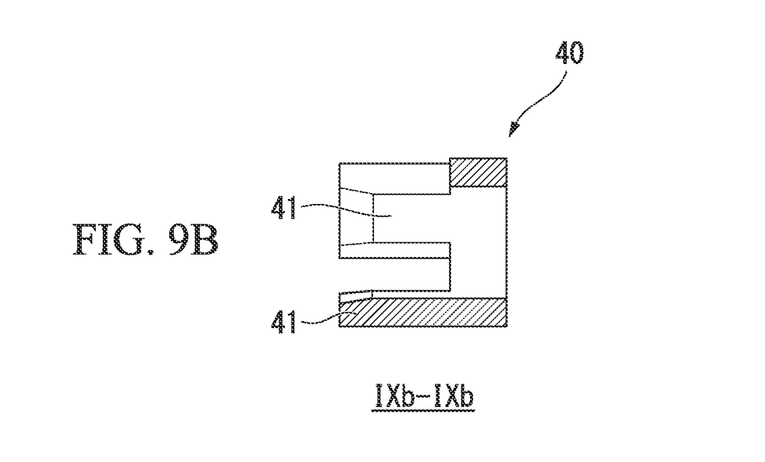
FIG. 9B is a longitudinal cross-sectional view (a cross-section along line IXb-IXb of FIG. 9A) showing the clamper.

FIG. 9A is a bottom-view showing the clamper 40. FIG. 9B is a longitudinal cross-sectional view (a cross-section along line IXb-IXb of FIG. 9A) showing the clamper 40.

The clamper 40 is a ring-shaped member. The clamper 40 is formed of titanium or titanium alloy. The outer diameter of the clamper 40 is about 1.5 mm. The outer diameter of the clamper 40 is a diameter slightly smaller than the smallest inner diameter of the inverse tapered hole portion 15 of the central hole 13 of the implant body 10. The clamper 40 may be forcibly put in the inverse tapered hole portion 15 by making the outer diameter of the clamper 40 a diameter slightly larger than the smallest inner diameter of the inverse tapered hole portion 15.

The inner diameter of the clamper 40 is about 1 mm. The inner diameter of the clamper 40 is externally fitted to the clamper pin 30. The clamper 40 is disposed at a position where it is caught on the engagement portion 31 of the clamper pin 30.

When the implant 5 has been assembled, the clamper 40 is disposed so as to be accommodated in the inverse tapered hole portion 15 of the central hole 13 of the implant body 10.

Three comb teeth 41 are formed on 1st end side (the +Z side) of the clamper 40. The comb teeth 41 are sites which are elastically deformed and spread toward the outer periphery side when the clamper 40 is put on the engagement portion 31 of the clamper pin 30. The comb teeth 41 of the clamper 40 act in the same manner as a so-called collet chuck.

When the comb teeth 41 of the clamper 40 are spread toward the outer periphery side, the comb teeth 41 form a diameter larger than the smallest inner diameter of the tapered hole portion 14. The clamper 40 is caught on (interposed in) the protruding site 15A that protrudes to the inner periphery side at an upper end of the inverse tapered hole portion 15 of the central hole 13 of the implant body 10. Thus, movement to the −Z side of the clamper 40 and the clamper pin 30 on which the clamper 40 is externally fitted is restricted.

Figure 10A:
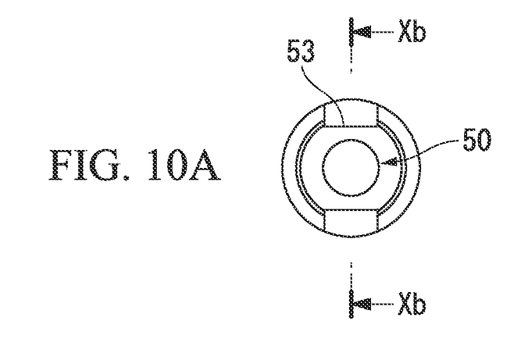
FIG. 10A is a top view showing a lock nut.
Figure 10B:
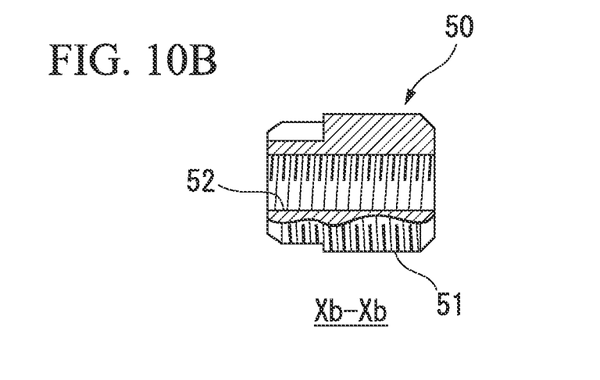
FIG. 10B is a longitudinal cross-sectional view (a cross-section along line Xb-Xb of FIG. 10A) showing the lock nut.

FIG. 10A is a top view showing the lock nut 50. FIG. 10B is a longitudinal cross-sectional view (a cross-section along line Xb-Xb of FIG. 10A) showing the lock nut 50.

The lock nut 50 is a ring-shaped member having an external thread 51 having a screw standard of M2.5 on the outer peripheral surface and an internal thread 52 having a screw standard of M1 on the inner peripheral surface. The lock nut 50 is formed of titanium or titanium alloy. The screw dimensions or the like of the external thread 51 and the internal thread 52 can be appropriately changed corresponding to the internal thread 25 and the external thread 32.

A pair of wrench grooves 53 having two faces facing in the opposite directions and parallel to each other is provided at the end face on the −Z side of the lock nut 50. It is possible to rotate the lock nut 50 by engaging a tool not shown (a wrench or the like) with two parallel faces of the wrench grooves 53.

The external thread 51 is screwed in the internal thread 25 formed at a portion of the through-hole 24 of the abutment 20. The internal thread 52 is screwed in the external thread 32 formed on 2nd end side (the −Z side) of the clamper pin 30. If the lock nut 50 is rotated to the clockwise direction in a state where the implant 5 has been assembled, the clamper pin 30 moves to the −Z side with respect to the abutment 20.

Implant Treatment on which an Operation is Performed Twice

Assembly of the implant 5 is performed according to the following procedure.

First, after the implant body 10 is embedded into the alveolar bone 2 of a patient in advance, the gum 4 is sutured. Although there are differences between individuals, osseointegration between the alveolar bone 2 and the implant body 10 is achieved over about three to six months.

The abutment 20 and all are attached separately from the implant body 10. The abutment body 8 is assembled by the abutment 20, the clamper pin 30, the clamper 40, and the lock nut 50.

The abutment body 8 is sold in an assembled form.

In the assembly of the abutment body 8, first, the clamper 40 is externally fitted onto the clamper pin 30. Next, the lock nut 50 is mounted with respect to the abutment 20. The external thread 51 of the lock nut 50 is screwed in the internal thread 25 formed at a portion of the through-hole 24 of the abutment 20.

Subsequently, the clamper pin 30 is inserted from the +Z side of the through-hole 24 of the abutment 20. When 2nd end side (the −Z side) of the clamper pin 30 comes into contact with the lock nut 50 mounted in the abutment 20, the clamper pin 30 is rotated to the clockwise direction. The external thread 32 of the clamper pin 30 is screwed in the internal thread 52 of the lock nut 50 by the rotation to the clockwise direction of the clamper pin 30. The clamper pin 30 is rotated to the clockwise direction until just before 1st end side (the −Z side) of the clamper 40 externally fitted onto the clamper pin 30 comes into contact with the end portion on the −Z side of the abutment 20.

Thus, the assembly of the abutment body 8 is completed.

Thereafter, the abutment body 8 is inserted into the central hole 13 of the implant body 10 embedded into the alveolar bone 2 of the patient. The tapered shaft portion 22 of the abutment 20 is fitted into the tapered hole portion 14 of the central hole 13 of the implant body 10 in a wedge form.

The engagement portion 31 on 1st end side (the +Z side) of the clamper pin 30 is inserted into the engagement hole portion 16 of the most bottom portion (the +Z side) of the central hole 13 of the implant body 10. The two parallel faces 31B of the engagement portion 31 of the clamper pin 30 come into close contact with (are fitted to) the two parallel faces 16A the engagement hole portion 16 of the implant body 10.

Next, a tool (a wrench) (not shown) is fitted into the wrench grooves 53 of the lock nut 50 and then rotated to the clockwise direction. The lock nut 50 moves in the +Z direction while being rotated. At the same time as this, the clamper pin 30 moves in the −Z direction.

At this time, since there is a difference between the external thread 51 (M2.5: 0.35 P) and the pitch (M1: 0.2 P) of the internal thread 52 of the lock nut 50, the amount of movement in the −Z direction of the clamper pin 30 becomes large, compared to the amount of movement in the +Z direction of the lock nut 50.

Since the engagement portion 31 of the clamper pin 30 is inserted into the engagement hole portion 16 of the implant body 10, and thus the two parallel faces 31B of the engagement portion 31 come into close contact with (are fitted to) the two parallel faces 16A of the engagement hole portion 16, rotation of the clamper pin 30 is restricted. The clamper pin 30 moves in the −Z direction without being co-rotated along with the lock nut 50.

If the clamper pin 30 is moved in the −Z direction, 2nd end side (the −Z side) of the clamper 40 externally fitted onto the clamper pin 30 comes into contact with the end portion on the +Z side of the abutment 20, and thus movement in the +Z direction of the clamper 40 is restricted.

In addition, if the clamper pin 30 is moved in the +Z direction, the tapered site 31A of the engagement portion 31 of the clamper pin 30 is inserted into the inner periphery side of the clamper 40 (the clamper 40 is put on the tapered site 31A). The three comb teeth 41 on the +Z side of the clamper 40 are elastically deformed and spread toward the outer periphery side.

Therefore, the clamper 40 is caught on the protruding site 15A that protrudes to the inner periphery side at the upper end of the inverse tapered hole portion 15 of the central hole 13 of the implant body 10, and thus movement to the −Z side of the clamper 40 and the clamper pin 30 is restricted.

In a state where the movement to the −Z side of the clamper 40 and the clamper pin 30 is restricted, the lock nut 50 is further rotated to the clockwise direction. The abutment 20 moves in the +Z direction. The abutment 20 further moves toward the implant body 10, and thus the tapered shaft portion 22 of the abutment 20 is further fitted into the tapered hole portion 14 of the central hole 13 of the implant body 10 in a wedge form.

In this way, the implant 5 is tightly assembled without rattling.

Thereafter, the artificial crown 6 is mounted on the outer peripheral surface on the −Z side of the abutment 20 of the implant 5 by using an adhesive or the like.

In the implant 5, the tapered shaft portion 22 is fitted (inserted) into the tapered hole portion 14, whereby the tapered shaft portion 22 and the tapered hole portion 14 function as a pressure-withstanding mechanism 60 that takes an external force (occlusal pressure F) acting on the abutment 20 (refer to FIG. 1), In particular, since the lengths in the Z direction of the tapered shaft portion 22 and the tapered hole portion 14 are sufficiently longer than in the related art, an area taking the occlusal pressure F becomes large, and thus the pressure-withstanding mechanism 60 has high pressure-withstanding performance. Therefore, for example, in a case where the implant 5 is used in a front tooth, or the like, even if the abutment 20 receives the occlusal pressure F from a direction intersecting the Z-axis direction, it is possible to reliably take the occlusal pressure F. Accordingly, neither crack nor chip is generated in the abutment 20 or the implant body 10.

When the abutment 20 is inserted into the central hole 13 of the implant body 10, the five projections 17 formed on the inner peripheral side surface of the tapered hole portion 14 of the central hole 13 of the implant body 10 are inserted into the five groove portions 23 formed in the outer peripheral side surface of the tapered shaft portion 22 of the abutment 20.

Since the projections 17 of the inner peripheral side surface of the tapered hole portion 14 are geared with the groove portions 23 of the outer peripheral side surface of the tapered shaft portion 22, rotation of the abutment 20 with respect to the implant body 10 is restricted. The projections 17 of the tapered hole portion 14 and the groove portions 23 of the tapered shaft portion 22 function as a rotation-preventing mechanism 70.

In the implant 5, the pressure-withstanding mechanism 60 (the tapered shaft portion 22 and the tapered hole portion 14) taking the occlusal pressure F and the rotation-preventing mechanism 70 (the projections 17 and the groove portions 23) are integrally formed. Therefore, the pressure-withstanding mechanism 60 can be formed longer (deeper) than in the related art. It is possible to make the length of the pressure-withstanding mechanism 60 (the tapered shaft portion 22 and the tapered hole portion 14) a length of ⅓ or more of the overall length of the implant body 10.

Therefore, the implant 5 can reliably take strong occlusal pressure F without occurrence of a crack or a chip in the abutment 20 or the implant body 10.

The technical scope of the invention is not limited to the above-described embodiment. The invention also includes configurations in which various changes are added to the above-described embodiment within a scope that does not depart from the gist of the invention. The specific materials, a layer configuration, or the like given in the embodiment are merely examples. Appropriate changes are possible.

A biocompatible ceramic material that forms the implant body 10 and the abutment 20 is not limited to zirconia (zirconium oxide). Alumina (aluminum oxide), yttrium oxide, hafnium oxide, silicone oxide, magnesium oxide, cerium oxide, or the like may also be adopted.

The implant body 10 and the abutment 20 may also be formed of a metal material such as titanium or titanium alloy.

A metal material that forms the clamper 40 is not limited to titanium having excellent biocompatibility. Titanium alloy may also be adopted. As for titanium alloy, for example, alloy of titanium and aluminum can be adopted. The clamper 40 may also be formed of an elastic body material such as resin (rubber).

The number of comb teeth 41 of the clamper is not limited to a case of being three. A case of being two or four or more is also acceptable.

A case has been described where the two parallel faces 16A and the two parallel faces 31B are respectively formed at the engagement hole portion 16 of the implant body 10 and the engagement portion 31 of the clamper pin 30 and are fitted to each other. However, there is no limitation thereto. In place of the two parallel faces 16A and the two parallel faces 31B, a polygonal hole portion and a polygonal shaft portion are also acceptable.

The implant 5 is not limited to a case of being used in dental treatment. The implant 5 may be used in a fracture treatment method or in an artificial joint.

REFERENCE SIGNS LIST

5: implant
8: abutment body
10: implant body
12: male screw
13: central hole
14: tapered hole portion (fitting hole portion)
15: inverse tapered hole portion
15A: protruding site (separation prevention hole portion)
16: engagement hole portion 16A: two parallel faces (co-rotation restriction hole portion)
17: projection (protrusion portion)
20: abutment
21: main body portion
22: tapered shaft portion (fitting shaft portion)
23: groove portion
24: through-hole
25: internal thread
30: clamper pin
31: engagement portion
31A: tapered site (separation prevention shaft portion)
31B: two parallel faces (co-rotation restriction shaft portion)
32: external thread
40: clamper
41: comb tooth
50: lock nut
51: external thread
52: internal thread
53: wrench groove
60 (14, 22): pressure-withstanding mechanism
70 (17, 23): rotation-preventing mechanism
F: occlusal pressure

The invention claimed is:

1. An implant comprising:
an implant body in which a fitting hole portion having a taper shape, an inner diameter of which is reduced over a depth direction, is formed in a portion of a central hole;
an abutment having a fitting shaft portion having a taper shape, which is fitted into the fitting hole portion;
a clamper pin which is inserted into a through-hole formed along the axial direction of the abutment and has a co-rotation restriction shaft portion that is engaged with a co-rotation restriction hole portion formed in the central hole of the implant body such that rotation of the clamper pin around a central axis of the clamper pin is restricted;
a lock nut which has an external thread that is screwed in an internal thread formed at a portion of the through-hole of the abutment and an internal thread that is screwed in an external thread formed at a portion of the clamper pin and which moves the clamper pin relative to the abutment; and
a clamper which is interposed between the clamper pin and the central hole of the implant body, and engaged with a separation prevention shaft portion of the clamper pin and a separation prevention hole portion of the implant body as the clamper pin moves relative to the abutment, thereby restricting relative movement between the clamper pin and the implant body.

2. The implant according to claim 1, wherein each of the implant body and the abutment is formed of ceramic.

3. The implant according to claim 1, wherein each of the implant body and the abutment is formed of zirconia.

4. The implant according to claim 1, wherein each of the clamper pin, the clamper, and the lock nut is formed of titanium or titanium alloy.

5. The implant according to claim 1, wherein a pressure-withstanding mechanism formed of the fitting hole portion and the fitting shaft portion and a rotation-preventing mechanism that prevents rotation of the abutment with respect to the implant body are integrally formed with each other, wherein the rotation-preventing mechanism includes: a plurality of protrusion portions formed along the depth direction on an inner peripheral surface of the fitting hole portion; and a plurality of groove portions which are formed along an axial direction in an outer peripheral surface of the fitting shaft portion and into which the plurality of protrusion portions are respectively inserted.

6. The implant according to claim 5, wherein the length of the pressure-withstanding mechanism is formed to be a length of ⅓ or more of the overall length of the implant body.

7. The implant according to claim 5, wherein the cross-sectional shape perpendicular to the depth direction of each of the plurality of protrusion portions, and the cross-sectional shape perpendicular to the axial direction of each of the plurality of groove portions, are formed in an arc shape.

* * * * *